United States Patent
Beulertz et al.

(10) Patent No.: US 10,036,298 B2
(45) Date of Patent: Jul. 31, 2018

(54) METHOD FOR DETECTING THE DEGREE OF AGING OF CATALYTIC CONVERTERS

(71) Applicant: UMICORE AG & CO. KG, Hanau-Wolfgang (DE)

(72) Inventors: Gregor Beulertz, Bayreuth (DE); Martin Votsmeier, Weinheim (DE); Ralf Moos, Bayreuth (DE)

(73) Assignee: UMICORE AG & CO. KG, Hanau-Wolfgang (DE)

( * ) Notice: Subject to any disclaimer, the term of this patent is extended or adjusted under 35 U.S.C. 154(b) by 0 days.

(21) Appl. No.: 15/311,277

(22) PCT Filed: May 8, 2015

(86) PCT No.: PCT/EP2015/060238
§ 371 (c)(1),
(2) Date: Nov. 15, 2016

(87) PCT Pub. No.: WO2015/173150
PCT Pub. Date: Nov. 19, 2015

(65) Prior Publication Data
US 2017/0107887 A1    Apr. 20, 2017

(30) Foreign Application Priority Data
May 16, 2014  (DE) .......... 10 2014 209 305

(51) Int. Cl.
G01N 33/20    (2006.01)
G01N 22/02    (2006.01)
(Continued)

(52) U.S. Cl.
CPC .......... *F01N 11/002* (2013.01); *G01N 22/02* (2013.01); *G01N 27/227* (2013.01);
(Continued)

(58) Field of Classification Search
CPC ............ G01N 22/02; G01N 33/20
(Continued)

(56) References Cited

U.S. PATENT DOCUMENTS 4,580,441 A    4/1986 Sakurai et al.
4,766,081 A *  8/1988 Ruckert ............. G01N 22/00
                                                        436/144

(Continued)

FOREIGN PATENT DOCUMENTS

DE    101 03 772 A1    9/2002
DE    10358495 A1    7/2005
(Continued)

OTHER PUBLICATIONS

Reiss, S. et al, Chemical Engineering Technology 2011, 34, 791-796.*
(Continued)

*Primary Examiner* — Arlen Soderquist
(74) *Attorney, Agent, or Firm* — Smith, Gambrell & Russell, LLP

(57) ABSTRACT

The invention is directed to a method for determining the state of aging of a catalytic converter (2). The disclosed method functions in a non-contacting manner as resonances formed when the catalytic converter (2) located in a housing is excited with high-frequency electromagnetic waves are analyzed.

5 Claims, 2 Drawing Sheets

Figure 1:
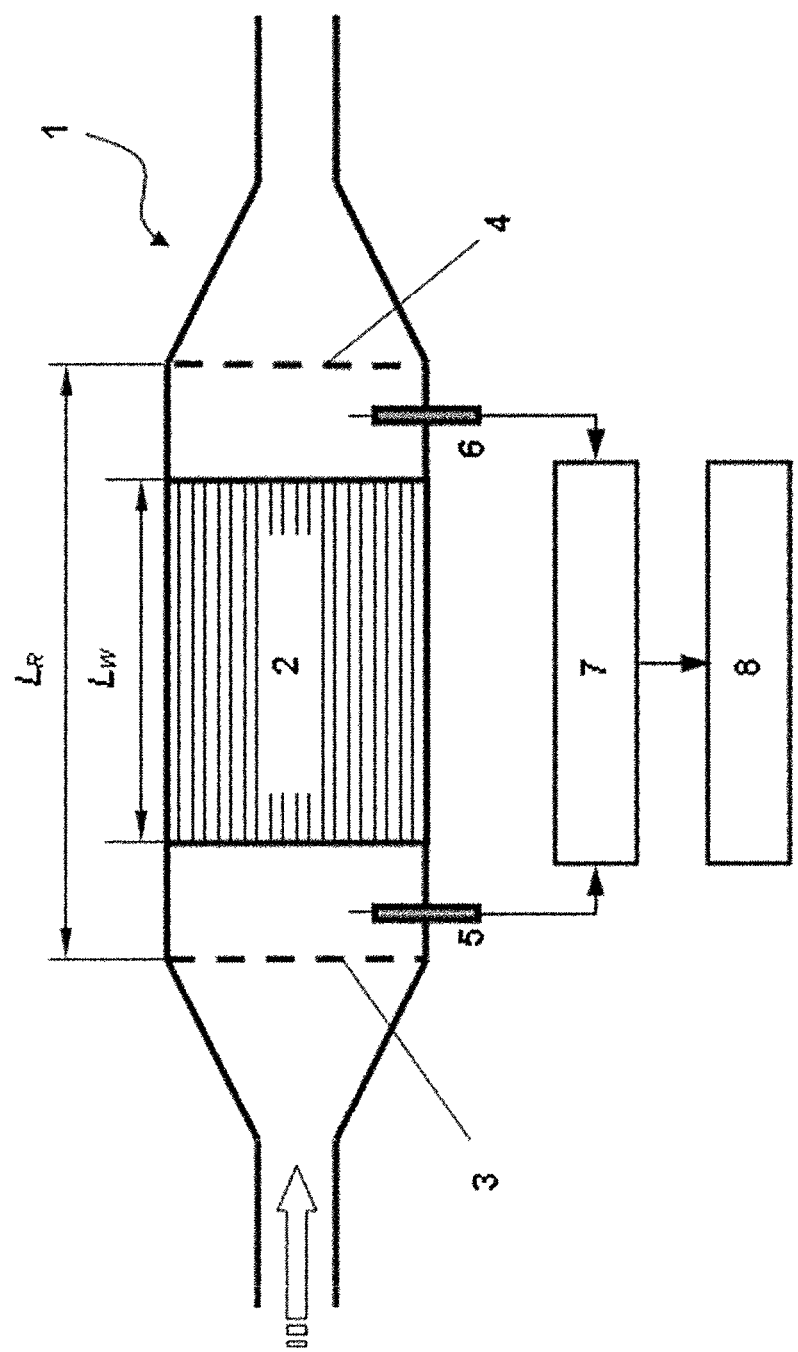

(51) Int. Cl.
*F01N 11/00* (2006.01)
*G01N 27/22* (2006.01)

(52) U.S. Cl.
CPC .... *F01N 2550/02* (2013.01); *F01N 2560/028* (2013.01); *F01N 2560/06* (2013.01)

(58) Field of Classification Search
USPC .......................................................... 436/37
See application file for complete search history.

(56) References Cited

U.S. PATENT DOCUMENTS

| | | | |
|---|---|---|---|
| 5,423,180 | A | 6/1995 | Nobue et al. |
| 6,655,129 | B2 | 12/2003 | Lindner et al. |
| 8,339,637 | B2 * | 12/2012 | Nakazato ................ G06F 3/121 358/1.14 |
| 9,540,984 | B2 | 1/2017 | Roesch et al. |
| 2007/0022746 | A1 | 2/2007 | Decou et al. |
| 2007/0101705 | A1 | 5/2007 | Knitt |
| 2008/0018442 | A1 | 1/2008 | Knitt |
| 2009/0033993 | A1 * | 2/2009 | Nakazato ................ G06F 3/121 358/1.15 |
| 2009/0229581 | A1 | 9/2009 | Ikeda |
| 2010/0186384 | A1 | 7/2010 | Gonze et al. |
| 2010/0212299 | A1 | 8/2010 | George et al. |
| 2012/0020875 | A1 * | 1/2012 | Matsuo .............. B01D 53/9418 423/700 |
| 2013/0023699 | A1 * | 1/2013 | Macht ................. B01J 23/8872 568/449 |
| 2014/0283503 | A1 | 9/2014 | Roesch et al. |
| 2014/0331752 | A1 | 11/2014 | Hall et al. |
| 2015/0355110 | A1 * | 12/2015 | Sappok .................... G01N 1/44 324/639 |
| 2016/0032850 | A1 | 2/2016 | Sunley et al. |

FOREIGN PATENT DOCUMENTS

| | | |
|---|---|---|
| DE | 102008012050 A1 | 9/2009 |
| DE | 102010034983 A1 | 2/2012 |
| DE | 102011107784 A1 | 1/2013 |

OTHER PUBLICATIONS

Hao, L. et al, Nanotechnology 2012, 23, paper 285706, 5 pages.*
Feulner, M.et al, Messungen zum Einfluss von Wasser auf die Beladungserkennung von Dieselpartikelfiltern mit Mikrowellentechnik. In Proceedings of the 11th Dresdner Sensor-Symposium, Dresden, Germany, Dec. 9-11, 2013; Gerlach, G., Schütze, A., Eds.; pp. 239-242.*
Reiss, S. et al, Sensor Letters, 2011, 9, 316-320.*
International Search Report for PCT/EP2015/060238, dated Aug. 3, 2015 in English and German Language.
R. Moos, M. Wedemann, M. Spörl, S. Reiß, G. Fischerauer, "Direct Catalyst Monitoring by Electrical Means: An overview on Promising Novel Principles", Topics in Catalysis, 52:2035-2040 (2009).
R. Moos, G. Gischerauer, "Automotive Catalyst State Diagnosis Using Microwaves", Oil & Gas Science and Technology—Rev. IFP Energies nouvelles, (2014).
Fischerauer, et al., Sensing the soot load in automotive diesel particulate filters by microwave methods, Measurement Science and Technology, vol. 21, Mar. 1, 2010, art. No. 35108. pp. 1-6.
Written Opinion of the International Searching Authority dated Nov. 19, 2015 for PCT/EPT015/060238 (10 pages).
International Preliminary Report on Patentability dated Nov. 22, 2016 for PCT/EP2015/060238 (12 pages).

* cited by examiner

METHOD FOR DETECTING THE DEGREE OF AGING OF CATALYTIC CONVERTERS

The present invention addresses a method for determining the degree of aging of a catalytic converter. The objective method functions free of contact by analyzing resonances that form upon excitation of the catalyst arranged within a housing with high-frequency electromagnetic waves.

Increasingly stringent exhaust gas laws, associated with the pressure to reduce fuel consumption, necessitate new approaches for both the internal combustion engine as well as for the treatment of its exhaust gas. This also means new approaches for controlling and monitoring emission control systems.

For example, in gasoline engines (what are known as $\lambda=1$ engines), the air/fuel ratio $\lambda$ (also called the air ratio) of the untreated exhaust gas is detected by means of a first $\lambda$ sensor. In the event of a control deviation from the nominal value $\lambda=1$, the air/fuel ratio is adjusted. $\lambda=1$ must be more or less maintained on average over time. Given the oxygen storage capacity of what is known as the "three-way catalytic converter" arranged following the first $\lambda$ sensor, an optimum conversion always occurs as long as the catalytic converter is still in a good state. As the quality of the catalytic converter decreases—which inter alia is manifested by a reduction of the conversion rate of the harmful exhaust gases HC, CO and NO and a rise in the start-up temperature—the capability of the catalytic converter to store oxygen also decreases. A second $\lambda$ sensor arranged following the catalytic converter can detect this. Very complicated modeling is required for such an indirect method in which the state of the oxygen-storing catalytic converter is inferred from the signals of the two $\lambda$ sensors, which modeling in particular requires an engine operating state model (see for example J. Riegel et al., "Exhaust gas sensors for automotive emission control", Solid State Ionics 152-153 (2002), 783-800).

Other types of catalytic converters—such as diesel (oxidation catalytic converters), coated particle filters, NOx storage catalytic converters and SCR catalytic converters—are subject to aging phenomena which cause their conversion efficiency to decrease continuously over the time of operation. Appropriate monitoring by means of OBD measures is therefore essential in order to be able to identify and, if necessary, exchange catalytic converters that can no longer sufficiently handle exhaust gas.

Assistance in this regard is provided in particular by methods in which the operating state and quality of a catalytic converter can be directly determined, in particular during regular operation. The degree to which the functionalities of a catalytic converter are still available can thus be determined, as for example, R. Moos, M. Wedemann, M. Spörl, S. Reiß, G. Fischerauer, "Direct Catalyst Monitoring by Electrical Means: An Overview on Promising Novel Principles", Topics in Catalysis, 52 (2009), 2035-2040 were able to demonstrate. High-frequency-assisted systems—as for example disclosed in DE102011107784A1, DE102008012050A1 or DE10358495A1—have a particularly simple design.

In the application DE10358495A1, a contact-free method is proposed for recognizing the state of a catalytic converter, in particular a NOx storage catalytic converter. For this purpose, an electromagnetic microwave resonance is excited in the interior of the catalytic converter housing designed as a cavity resonator, and the shift in the resonance frequency and/or quality is observed. The reduction of the resonance frequency is taken as a measure of increasing NOx load in the storage material. Once a predeterminable value of the resonance frequency is reached, a regeneration is performed.

In DE102008012050A1, an electromagnetic microwave resonance is excited in the interior of the catalytic converter housing designed as a cavity resonator and, for example, the position of the resonance frequency is observed. The change in the resonance frequency is, for example, taken as a measure of the oxygen load in the storage material of the catalytic converter.

It would be desirable to have a generally applicable, similarly simple and robust method available by means of which the quality or conversion efficiency of, if possible, all automotive exhaust gas converters can be sufficiently and reliably determined.

These and other objects that are obvious from the prior art to a person skilled in the art are achieved by a method having the features of the present invention. Also presented are some preferred embodiments of the method according to the invention.

In a very advantageous manner which is nonetheless successful in achieving the object addressed, the adsorption of water on the catalyst surface is determined using resonance characteristics at a catalytic converter temperature of <200° C., and the age of the catalytic converter is thereby inferred in a method for noninvasive detection of the aging of an automotive exhaust gas converter which is located in a metallic catalytic converter housing by emitting an alternating electromagnetic field, preferably within the microwave range, and detecting the same.

The surface of an automotive exhaust gas converter changes due to thermal stress or contamination. In this process, the number of free surface locations at which reactions can occur decreases. In the event of contamination, the active centers are blocked, and in the event of thermal stress, both the finely distributed precious metals and carrier materials are sintered together. The surface thus decreases with age, and accordingly also its capability of chemically and physically adsorbing substances at the surface. The amount of free surface locations reduced by aging changes the amount of water that can be adsorbed at the surface. The amount of water that can be adsorbed at the surface furthermore depends on the proportion of water in the exhaust gas on the one hand and on the temperature on the other hand. The electromagnetic material parameters (electrical conductivity and permittivity or complex permittivity) of the catalytic converter, including the carrier material, change due to the sorption of water.

Consequently, the corresponding resonance characteristic is determined at a given temperature of the catalytic converter, or tracked over a defined temperature range (such as $df_{res}/dT$), and then compared with data of a younger or fresher state of the catalytic converter which may be saved in the ECU of the automobile. If the result shifts toward lower values, for example in the event of a change in the resonance frequency with the temperature, aging of the catalytic converter is assumed since it can absorb less water, and the cavity resonance frequency correspondingly changes. However, a sufficient differentiation only occurs below a temperature of 200° C. The measurement is therefore preferably performed at >50° C. and <200° C., preferably between 60° C. and 150° C., and especially preferably between 70° C. and 120° C. This temperature range is also advantageous because the state diagnostics described in DE10358495A1 are not applicable, at least for three-way catalytic converters, since the electrical properties barely change with the oxygen load within this temperature range (as illustrated in FIG. 4 of DE102011107784A1). In the method according to the invention, environmental influences should be excluded or corrected if possible, for example using the heating characteristic of the exhaust train. For example, the influence of the temperature can be corrected by a method as outlined in DE102011107784A1.

As already indicated, the resonance characteristic of the irradiated cavity changes during the operation of the vehicle with the sorption capability of the catalytic converter located therein. This in turn depends on its degree of aging. Preferably, the agent to be adsorbed is water; this of course naturally always exists in exhaust gas when fuel combustion occurs. Water furthermore has a high dielectric constant and changes the electromagnetic material parameters of the catalytic converter to a corresponding extent as sorption increases or decreases. The amount of the adsorbed water is also influenced by the water content in the exhaust gas in addition to the aging. Advantageously, the water content in the exhaust gas is therefore calculated in the engine control and taken into account when determining the degree of aging from the resonance signal. If the water content in the exhaust gas changes over time, the evaluation can be additionally improved by taking into account the finite sorption rate of water. Preferably, the method according to the invention is employed when there is a sufficient and optimally constant amount of water in the exhaust gas. Particularly preferably, the measurement is carried out when an exhaust gas mixture exists that contains 3-20 parts per volume of water, and preferably 5-15 parts per volume.

The electrical properties of the catalytic converter can be determined not just by using the resonance frequency but also by considering other resonance characteristics. Such characteristics are preferably selected from the group comprising the resonance frequency, amplitude, quality of the resonator (Q), losses, the parameters of the scatter matrix $S_{ij}$, the magnitude of the transmission factor, the width of the resonance peak or resonance trough, and other quantities derived from the S parameters (see DE102008012050A1). Particularly preferable in this context is the resonance frequency as well as the magnitude of the reflection parameter $S_{11}$ or of the transmission parameter $S_{12}$. Especially preferable in this context is evaluation using the resonance frequency (see FIG. 2). Various resonance modes can also be used. In particular those are preferred that react differently to different disturbance variables such as the temperature.

Automobile catalytic converters are normally characterized in that they offer a large surface on which chemical reactions occur faster due to finely distributed precious metals such as Pt, Pd or Rh. As also mentioned above, the present method is based on the fact that the resonance characteristics change with the increasing aging of a catalytic converter. The catalytic converters considered here are all those relevant to a person skilled in the art, since all catalytic converters are subject to the same principle. Those catalytic converters are preferred which are selected from the group comprising three-way catalytic converters, diesel oxidation catalytic converters (possibly catalytically-coated diesel particle filters), NOx storage catalytic converters and SCR catalytic converters. Particularly preferable in this context are three-way catalytic converters provided with an oxygen storage material.

In one preferred embodiment of the present invention, the catalytic converter is surrounded by a microwave reflector (3, 4) (DE102008012050A1). All materials are suitable for this which counteract the exhaust gas flow with an optimally low counterpressure and are nevertheless capable of reflecting the employed microwaves. A person skilled in the art is aware of the relevant devices. In case of doubt, simple metal grids are useful. This creates a resonator that is clearly defined in terms of high-frequency and is independent of the shape of the connecting pipes. This can be advantageous because the conical transitions between the catalytic converter housing and the connecting pipes, in particular at the gas inlet, are designed in consideration of flow and not reflection, for example so that gas is flushed uniformly through the ceramic honeycomb body. In principle, however, a corresponding metallic catalytic converter housing in which the catalytic converter is normally installed is suitable for this purpose. Operating without the reflection grid is accordingly possible but can, in certain circumstances, require greater effort due to the inversion of the relationship between the catalytic converter state and measured S parameters.

Preferably located before and after the catalytic converter (2) are the antenna(s) (5, 6) (FIG. 1) for sending and receiving the electromagnetic radiation, which advantageously lies within the microwave range. A method according to the invention is, however, also preferable in which an antenna is used that is located in a metallic catalytic converter housing. This transmits and receives the corresponding signals. The antennas can be selected according to the discretion of a person skilled in the art. Such equipment, as well as the signal detection unit and corresponding analysis unit, are sufficiently known to a person skilled in the art (such as from P. S. Neelakanta, Handbook of Electromagnetic Materials. CRC Press, Boca Raton etc., 1995 and S. H. Chao, Measurements of microwave conductivity and dielectric constant by the cavity perturbation method and their errors, IEEE Transactions on Microwave Theory and Techniques 33 (1985) 519-526, as well as the literature cited therein).

The present invention succeeds in determining the degree of aging of any type of exhaust gas catalytic converter in a particularly advantageous manner. Before the priority date, it was not known that a conclusion regarding the catalytic converter quality could be made by means of the water sorption capacity of the catalytic converter to be investigated within a specific temperature range. With the relevant method, a person skilled in the art is provided for the first time with a procedure by means of which he can noninvasively and directly determine the degree of aging of an automotive exhaust gas converter during normal driving conditions, in a manner that is kept relatively simple. In light of the known prior art, this was by no means obvious.

EXAMPLE

FIG. 1 shows the basic structure of an exhaust gas treatment system with a housing part (1) in which is installed a catalytic converter (2), a measuring system with two antenna (5, 6) (of which one is optional), control (7) and evaluation electronics (8), and an optional temperature sensor (see DE102008012050A1) as well as an optional reflector (3, 4).

Figure 2:
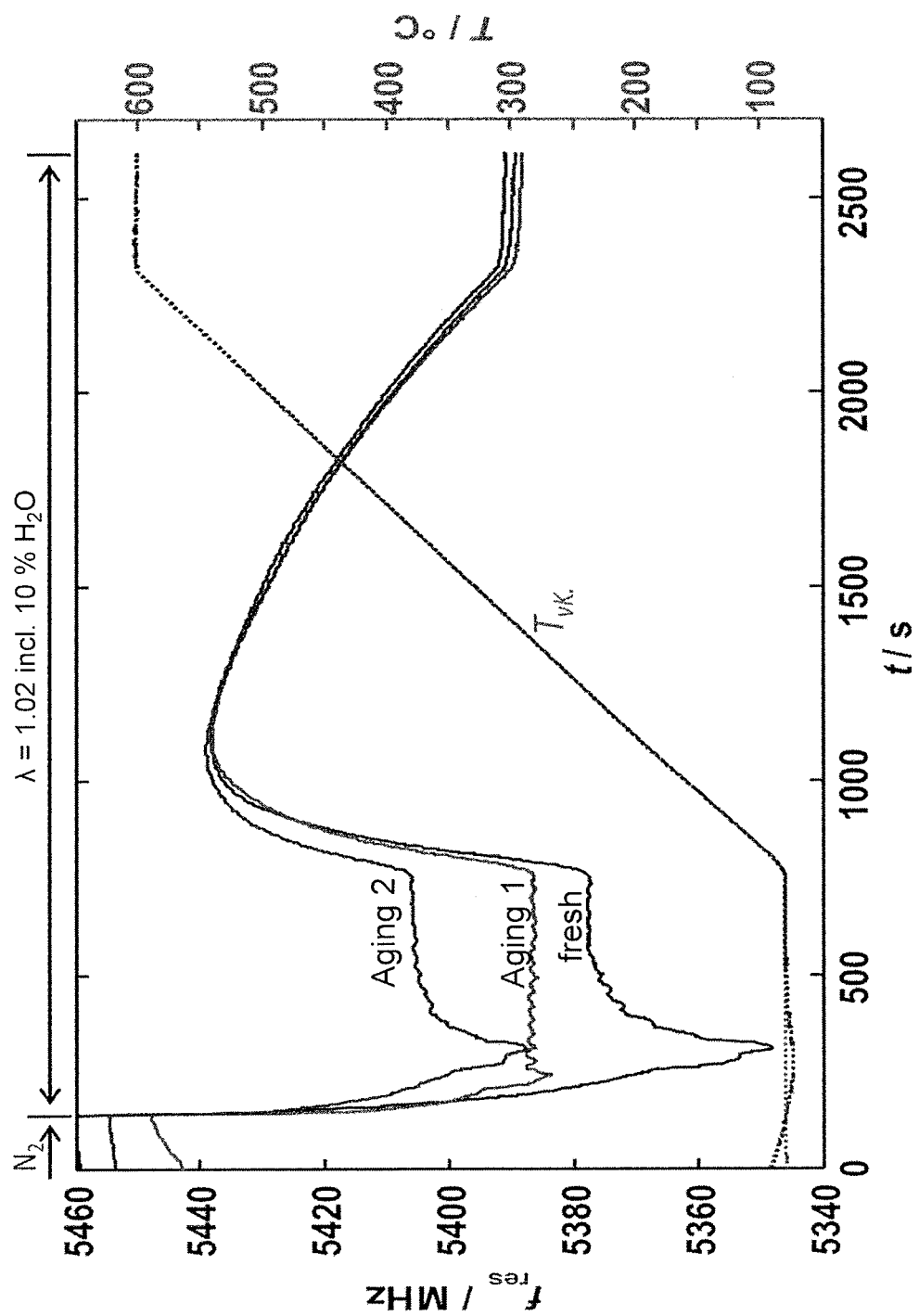

FIG. 2 shows resonance frequency curves which were measured in a synthesis gas plant for 1"×3" dia. TWC drill cores. A drill core was measured. This was first tested fresh, and after a 12 hour fuel cut aging at 850° C. (aging 1) as well as after an aging at 1050° C. (aging 2). In all three aging stages, the catalytic converter was first preconditioned with a temperature ramp (20 K/min) up to 600° C. under reducing conditions ($\lambda$=0.95) and then cooled in a nitrogen atmosphere to 80° C. During the actual test, a constant synthetic, lean exhaust gas ($\lambda$=1.02) with 10% $H_2O$ was set. In the beginning, the temperature was maintained for 600 s at 80°

C. and then increased at 20 K/min up to 600° C. The measured resonance frequency and the temperature of the catalytic converter in the three tests are plotted in FIG. 2. Upon switching from $N_2$ to the water-containing atmosphere, a significant change is discernible in the resonance frequency, depending on the degree of aging and the sorption properties of the catalytic converter that were thereby changed. Also dependent is the change in the resonance frequency with the temperature up to about 200° C.

From the measured data in FIG. 2, the change in the resonance frequency, for example, was evaluated with the temperature between 80 and 100° C. and resonance frequency at 80° C. (Table 1).

TABLE 1

|  | df/dT/MHz/K (between 80 and 100° C.) | $f_{res}$ (T = 80° C.)/MHz |
|---|---|---|
| fresh | 1.43 | 5377.4 |
| Aging 1 (850° C.) | 1.19 | 5386.7 |
| Aging 2 (1050° C.) | 0.85 | 5406.2 |

The invention claimed is:

1. A method for noninvasive detection of a degree of aging of an automotive exhaust gas converter via emission of an alternating electromagnetic field within a microwave range and detecting the same, wherein the automotive exhaust gas converter is located in a metallic catalytic converter housing and provided with an exhaust gas mixture containing water during measurement, and wherein adsorption of water on a catalyst surface is determined using certain microwave resonance characteristics at a catalyst temperature of <200° C., and the degree of aging of the catalytic converter is thereby inferred.

2. The method according to claim 1, wherein a catalyst temperature of >50° C. is used.

3. The method according to claim 1, wherein the exhaust gas mixture contains 3-20% by volume water.

4. The method according to claim 1, wherein the microwave resonance characteristics are selected from the group consisting of resonance frequency, amplitude, quality of a resonator (Q), losses, parameters of a scatter matrix $S_{ij}$, and quantities based thereupon (also at different frequency ranges).

5. The method according to claim 1, wherein an antenna located in the metallic catalytic converter housing is used to transmit and/or receive the alternating electromagnetic field.

* * * * *